United States Patent [19]

Twardzik et al.

[11] Patent Number: 4,737,580

[45] Date of Patent: Apr. 12, 1988

[54] PLATELET RELATED GROWTH REGULATOR

[75] Inventors: Daniel R. Twardzik, Bainbridge Island; George J. Todaro, Seattle, both of Wash.

[73] Assignee: Oncogen, Seattle, Wash.

[21] Appl. No.: 912,407

[22] Filed: Sep. 26, 1986

Related U.S. Application Data

[63] Continuation of Ser. No. 712,302, Mar. 15, 1985, Pat. No. 4,645,828, which is a continuation-in-part of Ser. No. 592,969, Mar. 23, 1984, Pat. No. 4,590,003.

[51] Int. Cl.[4] ............................................. C07K 15/06
[52] U.S. Cl. .................................................... 530/388
[58] Field of Search ................................ 530/387, 388

[56] References Cited

U.S. PATENT DOCUMENTS 4,585,742 4/1986 Bernal ................................. 530/387
4,618,585 10/1986 Chan ................................... 530/387

Primary Examiner—Delbert R. Phillips
Attorney, Agent, or Firm—Bertram I. Rowland

[57] ABSTRACT

Novel polypeptide compositions are provided which inhibit human tumor cell growth, which may or may not stimulate autophosphorylation of pp60 src and induce the release of a 52kDal polypeptide from neoplastic cells. Individual polypeptides may be isolated from mammalian blood platelets by selected extraction and purification procedures, may be synthesized or produced by hybrid DNA technology.

2 Claims, 1 Drawing Sheet

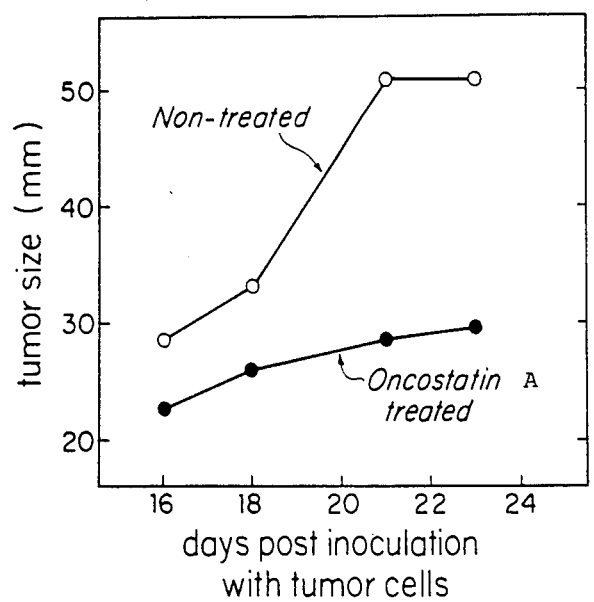

PLATELET RELATED GROWTH REGULATOR

CROSS-REFERENCE TO RELATED APPLICATIONS

This application is a continuation application of application Ser. No. 712,302, filed Mar. 15, 1985, now U.S. Pat. No. 4,645,828, issued Feb. 24, 1987, which is a continuation-in-part of application Ser. No. 592,969, filed Mar. 23, 1984, now U.S. Pat. No. 4,590,003, issued May 20, 1986, which disclosures are incorporated herein by reference.

BACKGROUND OF THE INVENTION

1. Field of the Invention

The complexity of the regulation of differentiation and proliferation of and by hematopoietic cells is becoming increasingly apparent as the list of factors which are isolated controlling these events continuously increases. For the most part, these factors are present in extraordinarily minute amounts in conjunction with numerous other proteins which serve a wide variety of functions. Factors which have been isolated and demonstrated to have activity include such polypeptides and proteins as γ-interferon, platelet-derived growth factor, colony stimulating factor, interleukin-2, erythropoietin, as well as numerous other lymphokines. There is substantial interest in the isolation, purification and characterization of these blood components because of their possible use in treatment, as well as their use in elucidating such diseases as cancer.

There are many pitfalls in isolating a naturally occurring factor. A system of separation must be developed which separates the desired factor from other factors which are present and may have similar characteristics. Secondly, some means for assaying the various fractions must be provided which specifically or substantially specifically characterizes the material of interest, in contrast to the other materials which are present. Where the polypeptide of interest has extraordinarily high activity, the difficulty of isolating the desired product is greatly enhanced. Thirdly, one must provide procedures which do not detrimentally affect the product of interest, particularly avoiding any denaturation. In addition, there are frequently other materials in the composition which may act upon the material of interest, changing it, so that the product which is ultimately obtained, which may have some of the desired activity, is not the naturally occurring material. Finally, after isolating the desired component in sufficiently pure form, one must then attempt to physically characterize the polypeptide, for example, by amino acid sequencing, glycosylation number, disulfide bridges, and the like. One must further characterize the material as to its physiological characteristics.

Finally, even after isolation of the purified compound, characterization of the compound's physiological activity may often prove to be elusive. Since in many situations the activity may be dependent upon the presence of one or more other compounds, a narrow concentration range, particular host cells, or the like, substantial intuitive effort as well as extended experimentation is frequently required to discover a compound's physiological activity and demonstrate the parameters affecting its activity.

2. Description of the Prior Art

Holley et al., *Proc. Natl. Acad. Sci. USA* (1980) 77: 5989-5992, describe the purification of epithelial cell growth inhibitors. Nelsen-Hamilton and Holley, ibid. (1983) 80: 5636-5640, describe the effect of a growth inhibitor and epidermal growth factor in the incorporation of radiotagged methionine into proteins secreted by African green monkey cells (BSC-1). Morgan et al., *Thromb. Haemost.* (1980) 42: 1652-60 provide the amino acid sequence for human platelet factor 4. Dawes et al., *Thromb. Res.* (1983) 29: 569-81 and Schernthaner et al., *Acta Med. Austriaca* [suppl.] (1979) 6: 375-9 report polyclonal antibodies to platelet factor 4. Lawler, *Thromb. Res.* (1981) 21: 121-7 compares the sequences and structures of β-thromboglobulin and platelet factor 4.

SUMMARY OF THE INVENTION

Polypeptide compositions and their use are provided which are characterized by having at least one of the following properties: capable of inhibiting tumor growth, while not inhibiting normal cell growth; capable of stimulating pp60 src autophosphorylation; capable of inducing secretion of a 52kDal protein from tumor cells; and having a substantially equivalent amino acid sequence of at least a portion of a polypeptide isolatable from mammalian platelets and exhibiting at least one of the previously-indicated properties. The polypeptides are provided in substantially pure form.

BRIEF DESCRIPTION OF THE DRAWING

FIG. 1 is a chart comparing the effect of Oncostatin-A on the growth of a tumor in athymic mice.

DETAILED DESCRIPTION OF THE SPECIFIC EMBODIMENTS

Compositions comprising polypeptides, derivatives, fragments, or analogs thereof and formulations containing such compositions are provided which effect mammalian neoplastic cell growth inhibition. The subject polypeptides are related to a naturally occurring polypeptide in the ethanolic HCl fraction obtained by extraction of platelets, called in the literature platelet factor 4 and referred to as Oncostatin-A hereafter. The polypeptides are stable at moderate temperatures (0°-25° C.), at a low pH, generally below about pH 3, usually at pH 2. The polypeptides have a molecular weight in the range of about 5,000-8,000, more exactly in the range of about 6,000-7,500, more particularly about 7,000. This polypeptide is obtained from platelets of higher mammals, particularly primates, more particularly humans.

The polypeptide compounds which are employed will have from about 15 to 80 amino acids, where the naturally occurring polypeptides and mimetic analogs thereof will have from about 60 to 75 amino acids, more usually from about 65 to 72 amino acids, while fragments will generally range from about 15 to 60 amino acids, more usually from about 15 to 35 amino acids. Of particular interest are polypeptides having from about 68 to 72 amino acids, more particularly 69, 70 or 71 amino acids. These polypeptides may be joined to other compounds, such as antigens, receptors, labels, or the like.

The polypeptides will have at least one biologically active sequence, e.g., immunological or epitopic, and may have more than one biologically active sequence, where such sequence can compete with a naturally occurring product for the biological property.

Compositions of interest will have an acidic (anionic) N-terminus and a basic (cationic) C-terminus, where the charged regions will be from 6 to 15 amino acids, usually 6 to 12 amino acids, where the region will include an amino acid sequence of from 6 to 8 amino acids where at least 50 number percent, usually at least 60 number percent are ionic amino acids and usually not more than 90 number percent are ionic amino acids. The ionic amino acids are: basic, K and R; acidic, D and E.

Those compositions having at least about 60 amino acids will have the charged domains separated by at least 25 amino acids, usually at least 40 amino acids and fewer than about 70, usually fewer than about 65 amino acids. The amino acid linking sequence separating the charged domains will usually have an excess of cationic over anionic amino acids, generally having from about a 1.5 to 3, usually about 2, to 1 ratio, with the pK of the compound in the range of about 6.5 to 8, particularly about 7.4.

There will usually be two disulfide bridges in the linking sequence, where the bridging disulfides are from about 20 to 45, usually 22 to 40 amino acids apart, preferably separated by about 25 and 39 amino acids. The cysteines proximal to the N-terminus will be from about 8 to 16 amino acids from the N-terminus, with the cysteines proximal to the C-terminus about 12 to 45 amino acids, usually 16 to 40 amino acids, from the C-terminus.

Compositions of interest will usually have a sequence proximal to the N-terminus, which has the formula of the pentapeptide E-A-E-E-D, more usually the decapeptide E-A-E-E-D-G-D-L-Q-C, frequently the pentadecapeptide E-A-E-E-D-G-D-L-Q-C-L-C-V-K-T, and more frequently having the following formula: E-A-E-E-D-C-D-L-Q-C-L-C-V-K-T-T-S-Q-V-R-P-R-H- where the letters have the following meaning in accordance with convention:

A—alanine
C—cysteine
D—aspartic acid
E—glutamic acid
G—glycine
H—histidine
L—leucine
P—proline
Q—glutamine
R—arginine
S—serine
T—threonine
V—valine Compositions of interest will usually have proximal to the C-terminus, a sequence of the formula K-K-I-I-K-K, more usually a sequence of the formula K-K-I-I-K-K-L-L, and preferably P-L-Y-K-K-I-I-K-K-L-L-E-S.

It should be understood that conservative substitutions of amino acids may be made. Conservative changes include substitutions involving D and E; F and Y; K and R; G and A; N and Q; V, I and R, and the like. In some instances, non-conservative exchanges will be desirable, for example, substituting K or R with N or Q. This substitution is of particular interest where a dibasic amino acid protease cleavage site is present, e.g., K-R, where the substitution protects the site against proteolytic cleavage.

Also, insertions or deletions may be involved, where usually insertions or deletions will involve from 1 to 2 amino acids, particularly 1 amino acid.

Novel polypeptides of interest will for the most part have the following formula:

$$Ac_R - M_R - Ba_r$$

wherein:

$Ac_R$ (acidic region) is the N-terminal region and is characterized by having from 10 to 20 amino acids of which from four to five are acidic, at least two of the first three amino acids are acidic, two acidic amino acids are in tandem and a different two acidic amino acids are separated by a neutral aliphatic amino acid; two cys residues are present separated by a single neutral aliphatic amino acid; the cys-X-cys is separated from D or E-X-D or E by from two to six amino acids;

$M_R$ is the middle region, either being a short linking group of from 2 to 30 carbon atoms, or having from about 25 to 40 amino acids; having two cysteines separated from the cysteines of $Ac_R$ by at least 10, usually at least 20, amino acids and each of these cysteines forming a disulfide bridge with one of the cysteines in $Ac_R$; having from five to seven basic amino acids and from two to five, usually three to four, acidic amino acids;

$Ba_R$ (basic region) is the C-terminal region and is characterized by having from 12 to 30 amino acids; having two pairs of basic amino acids each succeeded by from two to three neutral aliphatic amino acids, either polar or non-polar, usually non-polar; having a proline from 10 to 15 amino acids from the C-terminal amino acid.

Desirably $Ac_R$ will have the following formula:

$$(H)-aa^1-aa^2-aa^3-\overset{D}{\underset{E}{|}}-X^1-\overset{D}{\underset{E}{|}}-aa^6-\overset{D}{\underset{E}{|}}-aa^8-$$

$$-aa^9-X^2-C-aa^{11}-C-aa^{13}-\overset{K}{\underset{R}{|}}-X^3$$

wherein:

(H) intends hydrogen at the N-terminus;

$aa^{1,3}$ may be a bond or an aliphatic amino acid of from 2 to 6 carbon atoms, usually an acidic amino acid or a non-polar amino acid of from 2 to 3 carbon atoms;

$aa^2$ may be a bond or an aliphatic amino acid of from 2 to 6 carbon atoms, usually a basic amino acid, polar amino acid of from 3 to 5 carbon atoms, or a non-polar amino acid of from 2 to 3 carbon atoms;

$X^1$ is a bond or amino acid sequence of from 1 to 2 amino acids of from 2 to 6, usually 4 to 6 carbon atoms, which are aliphatic non-polar or polar amino acids;

$aa^6$ is an aliphatic amino acid of from 2 to 6, usually 2 to 4 carbon atoms which may be non-polar or polar, or an acidic amino acid;

$aa^8$ is an aliphatic amino acid of from 2 to 6, usually 5 to 6 carbon atoms, usually non-polar;

$aa^9$ is an aliphatic amino acid of from 2 to 6, usually 4 to 6 carbon atoms, particularly polar carboxamide substituted or basic;

$X^2$ is a bond or an amino acid sequence of from 1 to 2 aliphatic amino acids of from 2 to 6 carbon atoms particularly neutral amino acids;

$aa^{11}$ is an aliphatic amino acid of from 2 to 6, usually 3 to 6 carbon atoms, which may be non-polar or polar;

$aa^{13}$ is an aliphatic amino acid of from 2 to 6, usually 5 to 6 amino acids, particularly non-polar;

$X^3$ is a bond, an hydroxyl, alkoxyl group of from 1 to 3 carbon atoms, amino, or an amino acid sequence of from 1 to 6, usually 1 to 3 amino acids, usually neutral aliphatic and either non-polar or polar, particularly polar, the first three amino acids normally being neutral, wherein $X^3$ may terminate the molecule or be a link to $M_R$, $Ba_R$ or an antigen.

Preferred amino acids for the symbols are as follows:

$aa^1$—bond, D, E, G, A
$aa^2$—bond, G, A, K, R, S, T
$X^1$—bond, $(S \text{ or } T)_a$—$(V, L \text{ or } I)_a$ a is 0 or 1
$aa^6$—S, T, G, A, D, E
$aa^8$—V, L, I
$aa^9$—N, Q, K, R
$X^2$—$(G \text{ or } A)_a$—$(D \text{ or } E)_a$—$(V, L \text{ or } I)_a$
$aa^{11}$—V, L, I, M, S, T
$aa^{12}$—V, L, I
$X^3$—bond—$(S \text{ or } T)_b$—$(G, A, N \text{ or } Q)_a$—$(V, I, \text{ or } L)_a$—$(K, R, N, Q, H, F \text{ or } Y)_a$
b is an integer of from 0 to 3.

Desirably $Ba_R$ will have the following formula:

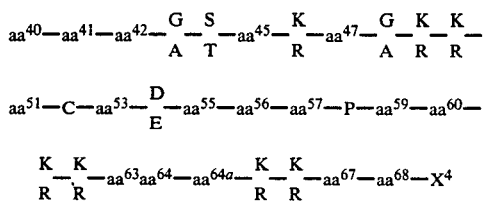

wherein:

$aa^{40,56}$ are an aliphatic acidic amino acid or amide thereof of from 4 to 5 carbon atoms;
$aa^{41,42,51,53,63,64,67}$ are aliphatic amino acids, particularly non-polar, of from 2 to 6, more particularly of from 5 to 6 carbon atoms;
$aa^{45}$ is an aliphatic amino acid of from 2 to 6 carbon atoms, particularly non-polar of from 4 to 6 carbon atoms, or a basic amino acid;
$aa^{47}$ is an aliphatic amino acid of from 3 to 5 carbon atoms, particularly polar, having hydroxyl or amide substituent, or acidic;
$aa^{55}$ is a neutral aliphatic amino acid of from 2 to 6 carbon atoms, either non-polar, particularly of from 4 to 6 carbon atoms, or polar of from 4 to 5 carbon atoms having a carboxamide functionality;
$aa^{57}$ is an aliphatic amino acid of from 2 to 6 carbon atoms, particularly non-polar of from 2 to 3 carbon atoms, or a basic amino acid;
$aa^{59}$ is an aliphatic amino acid of from 2 to 6, usually 4 to 6 carbon atoms, usually non-polar, or basic;
$aa^{60}$ is an aliphatic or aromatic amino acid, particularly if aliphatic of from 4 to 6 carbon atoms;
$aa^{64a}$ is a bond or an aliphatic polar amino acid of from 4 to 5 carbon atoms, particularly carboxamide substituted;
$aa^{68}$ is an aliphatic amino acid of from 2 to 6 carbon atoms, particularly non-polar;
$X^4$ is an hydroxyl, alkoxyl of from 1 to 3 carbon atoms, amino, or an amino acid sequence of from 1 to 4, usually 1 to 2, amino acids, particularly aliphatic amino acids, more particularly polar and acidic amino acids, having from 0 to 1 non-polar amino acid of from 2 to 3 carbon atoms, from 0 to 3 acidic amino acids, and from 0 to 3 hydroxyl substituted aliphatic amino acids, wherein $X^4$ may terminate the molecule or be a link to an antigen or immunoglobulin.

Of particular interest is where the symbols have the following definitions:

$aa^{40,56}$—D, E, N, Q
$aa^{41,42,51,53,63,64,67}$—V, L or I
$aa^{47}$—N, Q, S, T, D, E
$aa^{55}$—N, O, P, L, I, V; particularly P or L
$aa^{45,59}$—V, L, I, K, R
$aa^{60}$—V, L, I, F, H, Y
$aa^{64a}$—bond, N or Q
$aa^{68}$—G, A, P, L, I, V
$X^4$—$(G, A, D \text{ or } E)_a$—$(S, T, D, A, G \text{ or } E)_a$—$(D \text{ or } E)_c$—$(T \text{ or } S)_a$
c is 0 to 2.

(Where two amino acids are indicated at the same site, either amino acid may be present at that site.)

Desirably, $M_r$ will include a sequence of at least about 15 amino acids included in the following formula:

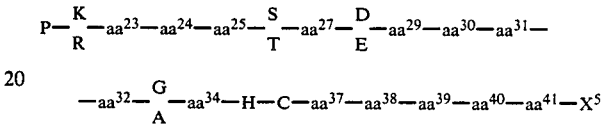

wherein:

$aa^{23}$ is an aromatic amino acid or an aliphatic polar amino acid of from 3 to 5 carbon atoms, particularly an amide substituted amino acid;
$aa^{24}$ is an aliphatic non-polar amino acid of from 2 to 6, usually 5 to 6 carbon atoms;
$aa^{25}$ is an aliphatic polar amino acid of from 3 to 5 carbon atoms, particularly an amide or hydroxyl substituted amino acid;
$aa^{27,29,30}$ are aliphatic non-polar amino acids of from 5 to 6 carbon atoms;
$aa^{31}$ is an aliphatic amino acid of from 2 to 6 carbon atoms, either non-polar of from 2 to 3 carbon atoms, or basic;
$aa^{32}$ is an aliphatic amino acid of from 2 to 6 carbon atoms, either non-polar of from 2 to 3 carbon atoms, or basic;
$aa^{34}$ is an aliphatic amino acid of from 2 to 6, usually 3 to 5 carbon atoms, which is non-polar or polar, particularly hydroxyl substituted;
$aa^{37}$ is an aliphatic amino acid of from 2 to 6, usually 3 to 5 carbon atoms, which is non-polar or polar, particularly proline or carboxamide substituted;
$aa^{38}$ is an aliphatic polar amino acid of from 3 to 5 carbon atoms, usually amide or hydroxy substituted;
$aa^{39}$ is an aliphatic non-polar amino acid of from 2 to 6 carbon atoms;
$aa^{40}$ is an aliphatic acidic amino acid or amide thereof of from 4 to 5 carbon atoms;
$X^5$ is a bond, hydroxyl, alkoxy of from 1 to 3 carbon atoms, wherein $X^5$ may terminate the sequence, be a link to $Ba_R$ or to an antigen.

Of particular interest are the following definitions for the symbols:

$aa^{23}$—F, H, Y, N, Q
$aa^{24,27,29,30}$—V, L, I
$aa^{25,38}$—S, T, N, Q
$aa^{31,32}$—G, A, K, R
$aa^{34}$—P, S, T
$aa^{37}$—P, N, Q
$aa^{38}$—S, T, N, Q
$aa^{39}$—G, A, P, V, L, I
$aa^{40}$—D, E, N, Q

The amino acids are categorized as follows:

|   |   |
|---|---|
| aliphatic | |
| neutral | |
| non-polar | G, A, P, V, L, I |
| polar | S, T, M, C, N, Q |
| acidic | D, E |
| basic | K, R |
| aromatic | F, H, Y, W |

As is evident from the above formulas, various conservative substitutions can be made in the above sequences without significantly affecting the physiological activity. Also, deletions and insertions of from 1 to 2 amino acids may be employed. Usually, not more than 5, usually not more than 3, changes (substitution, deletion or insertion) will be made in the above sequence.

Of particular interest for use in the subject invention are compounds having the following sequence:

```
Glu Ala Glu Glu Asp Gly Asp Leu Gln Cys Leu Cys Val Lys
Thr Thr Ser Gln Val Arg Pro Arg His Ile Thr Ser Leu Glu
Val Ile Lys Ala Gly Pro His Cys Pro Thr Ala Gln Leu Ile
Ala Thr Leu Lys Asp Gly Arg Lys Ile Cys Leu Asp Leu Gln
Ala Pro Leu Tyr Lys Lys Ile Ile Lys Lys Leu Leu Glu Ser
``` or analogs thereof, particularly analogs or fragments which include the four cysteines at approximately their respective positions and the 12 amino acids at or proximal to the C-terminus, particularly the 10 amino acids proximal to the C-terminus, and more particularly the 8 amino acids proximal to the C-terminus which includes four basic and four neutral aliphatic amino acids. Analogs of the above composition will usually have at least about 80%, more usually at least about 85%, and preferably at least about 90% of the same amino acids in the above sequence or portion of the above sequence.

The naturally occurring polypeptide compositions employed in this invention can be obtained in high purity as established by sensitive bioassays. The naturally occurring polypeptide compositions will have less than about 20%, more usually less than about 10%, and preferably less than about 5% by weight of polypeptides other than the major constituent present in the composition, which contaminating polypeptides are associated with platelets.

The polypeptides compositions of this invention demonstrate a variety of physiological activities. The subject compositions can be used to inhibit tumor growth in vitro and in vivo. The subject compositions can also be used to stimulate autophosphorylation of pp60 src. Subject compositions may thus serve as a substrate for the pp60 src enzyme and can be phosphorylated at the tyrosine position (residue 60) in the polypeptide. Also, tumor cells can be induced to release a 52 kDal protein when treated with Oncostatin-A. In addition, Oncostatin-A or analogs, fragments thereof, or fusion proteins containing sub-sequences (fragments) having competitive immunological properties can be used to produce monoclonal antibodies or act as a reagent in diagnostic assays for the detection of Oncostatin-A or immunologically competitive compounds or the presence of cell surface receptors for Oncostatin-A.

The subject compounds have high activity for tumor inhibition. The subject compositions can be used in vitro or in vivo for reducing the rate of growth of neoplastic cells. The polypeptide compositions can provide at 1 ng levels at least about 20% inhibition of tumor cell growth, particularly of carcinomas and sarcomas, e.g., of the lung, breast, skin, etc. Preferably, the polypeptide compositions will provide at least about 40%, and more preferably at least about 50%, inhibition of tumor cell growth in accordance with the colony inhibition test described in the Experimental section.

The subject compositions can be used in vivo by being administered to a host suspected of having neoplasia. The subject compositions can be applied to a neoplastic site, e.g., a melanoma, to reduce the rate of proliferation. Methods of application may include injection, introduction by catheter, direct application, or the like, depending upon the site of the tumor, the formulation of the subject composition, the dosage level and the like. Dosage will vary depending upon whether it is systemic or local, with dosage concentrations generally being from about 0.1 μg to 1,000 μg/Kg and total dosages for large mammals including primates of from about 0.01 to 10 mg per treatment dose.

Oncostatin-A like materials, including Oncostatin-A and its congeners (compounds sharing at least one physiological property of Oncostatin-A and including at least one amino acid sequence having substantially the same amino acid sequence of Oncostatin-A, where the congener may be of greater or lesser amino acid number than Oncostatin-A), can be formulated in physiologically acceptable carriers, such as phosphate buffered saline, distilled water, excipients, or the like, or may be employed neat.

Oncostatin-A and its congeners may be employed indirectly for detecting the presence of neoplastic cells. Where cells are subjected to concentrations of the active agent of from about 1 to 500 ng/ml, preferably from about 50 to 350 ng/ml of the active agent, a 52 kDal protein (p52) is secreted by the neoplastic cells. Thus, one could detect the presence of neoplastic cells by detecting the secretion of p52 into the external medium, e.g., nutrient medium, blood, urine, or other physiological fluid. Oncostatin-A can therefore be used to monitor the state of a host and the existence or absence of a neoplastic condition. Oncostatin-A can be used in diagnosing whether a tumor exists, in monitoring surgery, levels of metastasis, or the like. The Oncostatin-A like substance would be administered in vitro or in vivo (culture medium or host) in a sufficient amount to provide for induction of the secretion of p52. Fluid associated with the system would then be monitored for the presence of p52 as an indication of the presence of neoplastic cells.

Oncostatin-A like materials can also be used to stimulate the immune system, either by itself, but preferably in conjunction with other lymphokines, e.g., interferon, more particularly, γ-interferon. Thus, the Oncostatin-A like materials may be formulated with other polypeptides and administered to a host which is immunosuppressed, so as to stimulate the immune system. Gamma-interferon is known to induce Ia expression in monocytes and macrophages, as well as other tissues, such as endothelium and fibroblasts. The Oncostatin-A like materials induce Ia expression and stimulate the γ-interferon Ia induction, enhancing the efficacy of a given dose of γ-interferon. The amount of Oncostatin-A like materials will generally be employed to provide a concentration in the medium in the range of about 1 to 200, preferably about 2 to 70 ng/ml. The amount of γ-interferon will be conventional as to its use as a lymphokine, generally being in the range of about 0.5 to 200 ng/ml. Enhancements in expression of Ia of at least about 1.5, usually at least 2-fold, can be achieved with Oncostatin- A like materials, when used by itself or in conjunction with other lymphokines. Administration may be employed as described previously.

The Oncostatin-A like materials can also be used in conjunction with kinases, particularly pp60 src to change the substrate specificity of the enzyme. Particularly, by contacting the enzyme with small amounts of an Oncostatin-A like material, particularly at concentrations of from about 0.05 to 50 μg/ml, the kinase activity may be enhanced, including a change in the observed amino acids, which are phosphorylated, particularly, besides tyrosine being phosphorylated, serine is also phosphorylated. In this way, the combination of pp60 src or analogous kinases may be used for modifying polypeptides having tyrosine and serine amino acids, by providing for phosphorylation of both tyrosine and serine at enhanced rates.

The subject Oncostatin-A like materials may also be used as haptens or antigens, as haptens linked to an immunogenic potentiator, e.g., an antigen, particle or the like, for production of monoclonal antibodies or polyclonal sera. The antibodies can find wide use, particularly for diagnostic purposes. The antibodies may be used by themselves or in conjunction with Oncostatin-A like materials as reagents for the detection of Oncostatin-A and Oncostatin-A receptors, including antibodies to Oncostatin-A.

A wide variety of protocols and techniques are available for determining analytes of interest. These techniques involve a wide variety of labels, including enzymes, radionuclides, fluorescers, chemiluminescers, enzyme substrates, enzyme inhibitors, particles, and the like. The methods may involve a separation step (heterogeneous) or no separation step (homogeneous). The label may be covalently bonded to either the Oncostatin-A like material or the antibody to Oncostatin-A like material (anti-Oncostatin-A) or may be conjugated to an antibody directed to the anti-Oncostatin-A, for example, to the Fc of the anti-Oncostatin-A. The whole antibody may be used or fragments thereof, including Fab, F(ab)'$_2$, Fv, or the like. A number of United States patents have issued describing a wide variety of diagnostic techniques which may be used in this invention. Exemplary of a few of these patents are U.S. Pat. Nos. 3,766,162; 3,791,932; 3,817,837; 3,996,345; and 4,233,402. Particular types of assays include RIA, EIA, EMIT®, ELISA, SLFIA, FIA, all of which have found commercial application and for which reagents are available for other analytes. The various reagents may be provided in kits where the nature of the reagents and their relative amounts are selected for optimizing the sensitivity of the assay.

The antibodies may be prepared in conventional ways in accordance with the preparation of monoclonal antibodies or polyclonal sera. In each instance, an appropriate host will be injected with an immunogen having one or more epitopic sites of interest, usually followed by one or more booster injections. For polyclonal antisera, the host may be bled and the globulin fraction isolated. The globulin fraction may be further purified by affinity chromatography. For monoclonal antibodies, the host will be immunized as before, but in this instance the spleen will normally be removed and fused with an appropriate fusion partner. After selection of hybridomas expressing the desired antibody, the hybridomas will be subjected to limiting dilution, followed by selection and cloning, and further characterization.

The antibodies according to this invention may be any of the types which naturally occur, such as IgA, IgD, IgE, IgG and IgM, particularly IgM and the various subtypes of IgG, i.e., IgG1, 2, 3 or 4.

The resulting monoclonal antibodies can be used as immunogens for production of anti-iodiotype antibodies which will have conformational similarity to the Oncostatin-A type materials. These may then be used as substitute reagents for Oncostatin-A type materials in a variety of applications.

Oncostatin-A can be obtained by extraction of platelets with approximately 0.3M ethanolic hydrochloric acid. As inhibitors against degradation, phenylmethylsulfonyl fluoride and aprotinin may also be included, the former at levels of about 1–10% by weight of the extracting composition and the latter at levels of about 0.1–1 TIU/mg (TIU—trypsin inhibition units) of the extracting composition. After raising the pH to about 5, using aqueous ammonium hydroxide, a small amount of ammonium acetate is added and the solution clarified by centrifugation or other convenient means.

The protein is then precipitated by successively employing cold ethanol (95%) and ether, the precipitate collected and dialyzed against 0.1–0.5M acetic acid employing a dialysis membrane having a cutoff below about 3,000 Mr. The residue is lyophilized, resuspended in 1M acetic acid, clarified and is then ready for further purification by gel permeation chromatography employing Biogel P-10. The product is eluted with about 1M acetic acid and the various fractions monitored employing an appropriate assay technique, e.g., tumor growth inhibition.

The fractions having the growth inhibiting activity are lyophilized, resuspended in dilute aqueous trifluoroacetic acid, pH 2–3, clarified and then chromatographed on a high pressure, liquid chromatograph, where the silica packing has a coating of a long aliphatic chain of from about 16 to 20 carbon atoms, e.g., 18 carbon atoms. The column is equilibrated with dilute trifluoroacetic acid (0.02–0.1%) and the product eluted with an acetonitrile gradient of up to 60% acetonitrile in dilute (0.01–0.1, usually about 0.04–0.95%) trifluoroacetic acid. A relatively slow flow rate is employed, generally about 0.5 to 1 ml/min at ambient temperatures. The fractions may be assayed by the bioassay indicated previously or other bioassays. For further purification, the product obtained from the column may be purified utilizing high pressure gel exclusion chromatography.

The major peak of Oncostatin-A activity resolved by Novopak C$_{18}$ reverse phase liquid chromatography is lyophilized and resuspended in 100 μl of 40% acetonitrile containing 0.1% trifluoroacetic acid. The sample is injected into a hydroxylated polyether gel column (Bio Rad TSK-250) and eluted with a mobile phase consisting of 40% acetonitrile in 0.1% trifluoroacetic acid. Aliquots of each fraction are lyophilized and tested for Oncostatin-A activity; tumor cell inhibition activity coelutes with the major peptide peak (Rf-0.9), which also corresponds in molecular weight to that of the 6,000 Mr insulin marker used to calibrate this chromatographic system.

The product obtained from the column may be electrophoresed employing SDS-PAGE. The band at about 6,000–8,000 molecular weight is isolated. The band is shown to have strong growth inhibitory activity against neoplastic mammalian cells.

Instead of isolating Oncostatin-A from natural sources or synthesizing the polypeptide or its congeners on a solid support, Oncostatin-A may be prepared by hybrid DNA technology. The structural gene for Oncostatin-A can be obtained from the host cell genome employing probes prepared based on the amino sequence. A genomic library may be searched using the probe (which may be appropriately redundant), hybridizing fragments isolated and the fragments reduced in size and characterized by restriction mapping and sequencing.

Alternatively, a DNA may be searched analogously to the genomic library and if complete or partial structural genes isolated these can be used, the latter by employing an adapter to replace the missing codons.

Conveniently, a synthetic gene may be synthesized. By employing a synthetic gene substantial flexibility is achieved in that host preferred codons may be employed and unique or rare restriction sites may be introduced. The restriction sites may be introduced. The restrictin sites add a degree of flexibility in modifying various portions of the gene, introducing deletions, transitions, transversions, insertions, and the like. A strategy is devised employing single-stranded overlapping fragments which can be mixed together in a hybridizing ligating medium without interfering heteroduplex formation. The resulting double-stranded gene may then be cloned and purified. An exemplary sequence is set forth in the experimental section.

Desirably, the termini of the gene are different to ensure the proper orientation upon insertion. The gene may be inserted into an appropriate expression vector for expression. A large number of vectors are available for expression in prokaryotes and eukaryotes, such as fungi, e.g., yeast, mammalian cells, e.g., mouse cells, primate cells, etc. The replication system may be derived from plasmids, viruses or chromosomes. Illustrative replication systems include ColE1, lambda, RSF1010, 2 $\mu$m plasmid, SV40, adenovirus, papilloma bovine virus, etc.

Besides at least one replication system, where episomal maintenance is desired (no replication system is required if integration is desired), a marker will usually be present which allows for selection of the host containing the desired gene. The marker will usually provide biocide resistance, e.g., antibiotics or heavy metals or complementation, prototrophy to an auxotrophic host. One or more markers may be present, usually not more than three.

The structural gene will be located, usually by insertion into a polylinker (a sequence having a plurality of restriction sites), between transcriptional and translational initiation and termination regulatory regions recognized by the expression host. By appropriate choice of the transcriptional initiation region, transcription may be constitutive or inducible. A large number of promoter regions have been isolated and shown to be useful, such as the E. coli trp and lac promoter, the lambda $P_L$ and $P_R$ promoters, the yeast glycolytic enzyme promoters, the SV40 and adenovirus early and later promoters, and the like.

In addition, a fused gene may be prepared by providing a 5'-sequence to the structural gene which encodes a secretory leader and processing signal. Illustrative secretory leaders which have been described include the secretory leaders of penicillinase, $\alpha$-factor, immunoglobulins, T-cell receptors, outer membrane proteins, and the like. By fusion in proper reading frame the mature Oncostatin-A or congener may be secreted into the medium.

The construct containing the structural gene and flanking regions providing regulations of expression may be introduced into the expression host by any convenient means, e.g., transformation, with for example, calcium phosphate precipitated DNA, transfection, transduction, conjugation, microinjection, etc. The host may then be grown to a high density in an appropriate nutrient medium. Where the promoter is inducible, permissive conditions will then be employed, e.g., temperature change, exhaustion or excess of a metabolic product or nutrient, or the like.

Where the product is retained in the host, the cells are harvested, lysed and the product isolated and purified by extraction, precipitation, chromatography, electrophoresis, etc. Where the product is secreted, the nutrient medium may be collected and the product isolated by conventional ways, e.g., affinity chromatography.

Besides being used for expression the structural gene sequences may be used as probes for hybridization and detection of duplexing sequences. For example, the presence and amount of mRNA may be detected in host cells.

The followng examples are offered by way of illustration and not by way of limitation.

EXPERIMENTAL

Abbreviations: DMEM—Dulbecco's modified eagle's medium; PBS phosphate buffered saline; P/S—penicillin/streptomycin (0.57 mg/ml each); FCS—fetal calf serum; SDS-PAGE—sodium dodecylsulfate polyacrylamide gel electrophoresis.

PURIFICATION OF ONCOSTATIN-A

Acid-ethanol Extraction from Human Platelets

Fresh or frozen platelets (50 g wet weight) thawed at room temperature were resuspended in two volumes of: 375 ml ethanol (95%), 7.5 ml conc. HCl, 33 mg phenylmethylsulfonyl fluoride and 1 ml of aprotinin (23 TI-U/ml; from bovine lung—Sigma Chemical Co. A6012). The mixture was stirred at 4° C. overnight, centrifuged 8K rpm in Beckman-type 19 rotor for 30 min and the supernatant removed. The pH of the supernatant was adjusted with conc. ammonium hydroxide to 4.0 and the pH raised to 5.2 using a 1:10 dilution of conc. ammonium hydroxide. After adding 1 ml of 2M ammonium acetate (pH 5.2) per 0.1 of supernatant, the solution was centrifuged 8K rpm in type 19 rotor for 30 min. The supernatant was removed, a 2× volume cold 95% ethanol added, followed by a 4× volume cold diethyl ether and the mixture allowed to stand overnight at 0° C. The precipitate was collected by centrifuging at 8K rpm type 19 rotor for 30 min and the pellet was suspended in about 10-20 ml of 1M acetic acid. The acetic acid dispersion was dialyzed extensively against 5L×2 changes of 0.2M acetic acid in a Spectrapor dialysis membrane (#3) tubing (cutoff 3,500 Mr) (American Scientific Products). The extract was lyophilized, resuspended in 7.5 ml of 1M acetic acid, followed by centrifuging at 30K rpm.

Gel Permeation Chromatography

Biogel P-10 (200-400 mesh; Bio Rad Labs) was swelled overnight in 1M acetic acid, degassed thoroughly and then poured into a 100×2.5 cm siliconized glass column and allowed to equilibrate overnight with 1M acetic acid. All solutions were degassed before using.

The acid-ethanol solubilized peptides (50-70 mg of protein) from 25 g of human platelets were dissolved in 7.5 ml of 1M acetic acid and applied to the above column. Fractions (3.5 ml) were collected and aliquots were lyophilized and tested for inhibition of 5-$^{125}$I-iodo-2'-deoxyuridine incorporation into A549 human lung carcinoma cells.

Reverse-phase High-pressure Liquid Chromatography

The fraction containing the peak of tumor growth inhibitory activity (about 200 ng of protein) from the above column was lyophilized and resuspended in 0.05% (v/v) of trifluoroacetic acid. The column was then eluted with a linear 0.60% gradient of acetonitrile in 0.045% triluoroacetic acid at a flow rate of 0.8 ml/min at 23° C. Aliquots of each fraction were lyophilized and assayed in triplicate, as described above.

The fraction(s) containing the inhibitory activity were then dissolved in 40% acetonitrile containing 0.1% trifluoroacetic acid and applied to a hydroxylated polyether gel column (Bio Rad TSK-250) and eluted with a mobile phase of 40% acetonitrile in 0.1% trifluoroacetic acid. Fractions were collected, lyophilized and assayed in triplicate for growth inhibitory activity. The activity elutes in the fraction where the insulin marker elutes and corresponds to a molecular weight of 6-8 kDal.

Those fractions having the highest activity were then electrophoresed employing SDS-PAGE as follows.

The peptide corresponding to the major Oncostatin-A activity from the reverse phase HPLC purification step was lyophilized, resuspended and boiled (2 min) in 0.03 ml of a sample preparation buffer containing 12.5 mM Tris-Cl pH 6.7, 4% SDS, 10% $\beta$-mercaptoethanol, 20% glycerol and 0.01% bromphenol blue. The sample was loaded onto a 5% polyacrylamide stacking gel poured over a 17 to 27% polyacrylamide gradient slab gel containing 0.1% SDS, at pH 8.8. The get was run at 10 milliamps until samples migrated through the stacking gel and at 20 milliamps until the dye front migrated to the bottom of the gel. Gels were fixed and stained overnight in a solution of 0.2% Coomassie blue, 50% methanol and 9% acetic acid. Following destaining, Coomassie positive bands were localized utilizing a Hoffer densitometer. Markers included insulin (6,000 Mr), trypsinogen (24,500 Mr), RN'ase (13,700 Mr), and aprotinin (6,500 Mr). The major peptide comigrated with the 6,500 Mr aprotinin standard under these conditions of electrophoresis.

The assay employed was as follows: On day 2 in the morning A549 cells (human lung carcinoma) in Nunc 96 well plates (Kamstrupvej 90. DK-4,000, Roskilde, Denmark) were set up. These cells were passaged when there were fewer than 30. Into all but the peripheral wells was introduced 45,000 cells/50 $\mu$l/well ($9 \times 10^4$ cells per ml DMEM with 10% FCS, P/S, glutamine). The peripheral wells received 50 $\mu$l PBS and the entire plate was incubated at 37° C. In the afternoon, the test samples were resuspended in DMEM with 10% FCS, P/S, glutamine triplicate testing. Into each test well was delivered 50 $\mu$l, while control wells received 50 $\mu$l DMEM and the plate incubated at 37° C. for 3 days. On day 4, into each well 50 ml of a solution of $^{125}$-I-iodo-2'-deoxyuridine (4 Ci/mg-0.5 mCi/ml) (1 $\mu$l isotope/ml DMEM containing 10% FCS, P/S, glutamine) and the plate incubated at 37° C. overnight. On day 5, the medium was aspirated from the wells, washed 1× with PBS, 100 $\mu$l methanol added, the methanol allowed to stand for 10 min followed by aspiration of the methanol. To the wells was then added 200 $\mu$l, 1M sodium hydroxide, the plate incubated for 30 min at 37° C. and then 1M sodium hydroxide removed with Titertek plugs (Flow Labs). The plugs were then counted in a gamma counter for radioactivity.

To demonstrate the effectiveness of the Oncostatin-A prepared above, the following test was carried out. The test is referred to as soft agar colony inhibition. The materials employed are 5% agar (3.75 g Nobel agar (Difco)), 75 ml of distilled water autoclaved in a 125 ml Wheaton bottle, DMEM with 10% FCS, 100U penicillin, 100U streptomycin, 200 mM glutamine, and human melanoma cells (A375).

Materials to be tested are lyophilized in a sterile 12×75 mm test tube. A 1:10 dilution of the 5% agar is made with DMEM and heated to 46° C. in a water bath. A base layer is prepared by pipetting 1 ml of 0.5% agar solution into each well of a 6well culture plate (35×14 mm). The layer is allowed to stand at room temperature until it hardens. SA$_6$ cells are prepared by trypsinizing and the number of cells counted. The cells are diluted to a final concentration of $1 \times 10^4$ cells per ml and 0.35 ml of cells is added to each test sample tube.

Into each of ten test sample tubes is pipetted 0.750 ml of a 0.5% agar solution, the mixture vortexed gently and the contents of the test sample tube (test sample, cells, agar) is poured onto the base layer and allowed to stand for about 20 min at room temperature until the agar hardens. The plates may then be stored in a 37° C. humidified incubator with 5% carbon dioxide.

The plates are checked for inhibition of colony growth after 3 days and up to 10 days depending on the potency of the test material. The number of colonies is counted in 8 random low power microscope fields. When plates are to be maintained longer than 5 days, another 1 ml layer of 0.3% agar solution is overlayed on the test sample layer to prevent drying of the test sample layer.

The above procedure was employed using varying concentrations of the purified Oncostatin-A. The following table indicates the results, the amount of Oncostatin-A indicated being the lyophilized amount introduced into the test tube. The results are reported as percent maximal inhibition.

TABLE I

| Oncostatin-A log$_{10}$ng | Maximal Inhibition % |
| --- | --- |
| 0.8 | 45 |
| 0.26 | 73 |
| 20 | 81 |
| 60 | 100 |

It is evident from the above results, that the subject polypeptide is a potent inhibitor of cell growth. Based on the results observed with the melanoma cells, about 1 ng is sufficient to provide about 50% inhibition. The subject compound can, therefore, find a wide variety of uses in inhibiting cellular growth, including neoplastic cellular growth. For example, the subject compound also inhibits a variety of cultured human tumor cells, but not normal non-neoplastic human foreskin fibroblasts, as evidenced in the following table.

TABLE II

Effect of Oncostatin-A on in vitro DNA synthesis in cultured human cells

| Cell Line | % Maximal* inhibition of $^{125}$I-deoxyuridine incorporation |
| --- | --- |
| Transformed | |

TABLE II-continued
Effect of Oncostatin-A on in vitro DNA synthesis in cultured human cells

| Cell Line | % Maximal* inhibition of $^{125}$I-deoxyuridine incorporation |
|---|---|
| Human carcinoma of lung (A549) | 100 |
| Human adenocarcinoma of lung (H125) | 41 |
| Human melanoma (A375) | 67 |
| Human carcinoma of breast (MCF-7) | 37 |
| Non-transformed | |
| Human foreskin fibroblast (HuF$_{p6}$) | 0 |

*Utilizing the assay conditions described, the maximum inhibition of $^{125}$I-deoxyuridine incorporation into A549 cells observed at saturating concentrations of Oncostatin-A (100 ng/well) does not exceed 50% relative to untreated control cultures.

Effects of Oncostatin-A on the Growth of Human Cancer Cells in Athymic Mice

Young (8–10 weeks) athymic mice were injected subcutaneously in the inguinal region with $5 \times 10^6$ human lung carcinoma cells (A549) suspended in 100 μl of phosphate buffered saline (PBS). Seven days post inoculation palpable tumors developed 2.5–3.0 mm in diameter; tumor bearing mice were randomly selected from this population and injected on day 7 subcutaneously on the tumor site with 50 μl of PBS containing 0.30 μg of Oncostatin-A purified to homogeneity from human platelets, as described previously. Injection of tumor bearing control mice with PBS without Oncostatin-A did not effect tumor growth. Tumor bearing mice were than subsequently injected with an equivalent dose of Oncostatin-A in 50 μl of PBS at days 11 and 16 post-inoculation of A549 cells. These doses of Oncostatin-A were injected directly into the tumor mass utilizing a 30½″ g needle. Tumor size was monitored at the days indicated by measuring tumors in both the horizontal and vertical dimensions with calipers; (a) tumor size noted on the ordinate represents multiples of these two dimensions. The results are depicted in FIG. 1.

Specific Release of a 52,000 Mr Polypeptide by Oncostatin-A Treated with Human Lung Cancer Cells Human lung carcinoma cells (A549) were treated with Oncostatin-A (200 ng/ml of culture) and the effect on polypeptides released into the cell culture supernatant was determined. Treated and control cultures (no Oncostatin-A) were pulsed with $^{35}$S-methionine (5 μCi/ml S.A.—800 Ci/mmol) at time 0 (addition of Oncostatin-A or medium only (control)). Twelve hours later culture supernatants were removed and clarified first at low speed ($1,500 \times g$ for 15 min) than at high speed ($30,000 \times g$ for 1 hr). Polypeptides were precipitated from clarified supernatants with trichloroacetic acid (TCA) followed by sodium-dodecylsulfate polyacrylamide gel electrophoresis on 12.5% acrylamide slab gels.

Radioautography of the gel demonstrated the presence of a 52,000 Mr $^{35}$S-methionine labeled polypeptide in supernatants derived from A549 cells treated with Oncostatin-A, whereas untreated cancer cells released minimum amounts of this protein (at least a ten-fold increase was seen after Oncostatin-A treatment). No other qualitative or quantitative differences were seen between treated or control cultures.

Stimulation of pp60 src Autophosphorylation by Oncostatin-A pp60 src was purified by immunoaffinity chromatography as described (Erickson et al., *Proc. Nat. Acad. Sci. USA* (1979) 76:6260–6264; Erickson et al., *Cold Spring Harbor Symp. Quant. Biol.* (1979) 44:902–917. Five microliters of purified enzyme (approximately 0.47 pmoles) were incubated with 100 ng of purified homogenous Oncostatin-A in a final reaction volume of 30 μl containing 20 mM ATP, 5 mM MgCl$_2$, 10 mM Tris-Cl pH 7.2 for 30′ at 30° C. Reactions were terminated by the addition of 2× sample buffer and analyzed by SDS polyacrylamide gel electrophoresis as described (Laemmeli, U.K., *Nature* (1970) 227:680–685). Autoradiography of the slab gels indicated apparently a tenfold stimulation in autophosphorylation of pp60 src. The increase in phosphorylation was not restricted to tyrosine residues but was also found in serine positions in the src enzyme.

Effects of Oncostatin on Macrophage Ia Antigen Expression

Wehi-3 is a mouse macrophage cell line which can be induced by gamma interferon (γ-IFN) to express H2 class II antigens. The features of this induction have been studied by several laboratories and shown to be an accurate replica of normal macrophage induction. These cells were grown either with or without a low amount of γ-IFN with several concentrations of platelet Oncostatin-A. Both in the presence or absence of γ-IFN, Oncostatin-A showed a dose dependent enhancement of class II antigen as measured by direct immunofluorescence on a FACS. The magnitude of the Oncostatin-A effect was generally twofold at the concentrations employed ($\approx 2$–70 ng/ml).

PRODUCTION OF MONOCLONAL AND POLYCLONAL ANTIBODIES SPECIFIC FOR ONCOSTATIN-A

Cross-linking Oncostatin-A to Bacteria Lipopolysaccharide

The procedure for cross-linking Oncostatin-A to bacterial lipopolysaccharide is a modification of the method developed by Primi and Cazenave, *J. Immunol.* (1982) 129(3):1124–1129.

Ten ng of Oncostatin-A and 12.5 ng of bacterial lipopolysaccharide (LPS; Sigma #L-263) was diluted to a volume of 500 μl with distilled water. Fifty μl of 2.5% glutaraldehyde in PBS was added and the mixture was incubated for 30 min at room temperature. The reaction was stopped by adding 50 μl of 2M glycine in PBS and incubating the mixture at room temperature for 1 hr. The Oncostatin-A: LPS conjugate was diluted with 10 ml of mixed lymphocyte conditioned medium and a filter sterilized for use in an in vitro immunization.

In Vitro Immunization of Balb/C Splenocytes with Oncostatin-A and LPS Conjugate

Non-immune splenocytes were immunized in vitro using a modification of the procedure described by Reading, *Immunol. Meth.* (1982) 53:261–269.

Mixed lymphocyte conditioned (MLC) medium was prepared by culturing equal numbers of Balb/c and C57 black mouse thymocytes in DMEM containing 2% rabbit serum at $4 \times 10^6$ cells/ml for 48 hr. The medium was collected and stored at $-20°$ C.

Peritoneal exudate cells (PEC) were collected by flushing a thioglycollate treated Balb/c mouse with sterile PBS. The PEC cells were placed in culture with 1 mouse equivalent of splenocytes and 10 ml of MLC medium containing 10 ng of Oncostatin-A-LPS conjugate. The cells were cultured for 7 days.

Production of Monoclonal Antibodies

The immune splenocytes were collected and fused with SP2/0 myeloma cells at a ratio of 1:1 to produce hybridomas which synthesize Oncostatin-A specific monoclonal antibodies. The hybridomas were tested for production of Oncostatin-A antibodies by an enzyme linked immunoassay (ELISA). Positive hybridomas were cloned twice by limiting dilution. Clones were expanded, tested for immunoglobulin class, and injected into Balb/c mice for ascites production.

Forty positive hybridoma clones were initially expanded and retested for anti-Oncostatin-A activity. Seven of the most reactive clones were used to produce ascites fluid in Balb/c mice. The remaining clones were expanded and frozen. The ascites were tested for specificity against Oncostatin-A, an Oncostatin-A peptide-KLH conjugate and BSA in an ELISA. The ascites reacted with both Oncostatin-A and to a lesser extend Oncostatin-A peptide at dilutions of 1 to 3,000. The immunoglobulins were purified by caprylic acid precipitation method described by Russo, et al., *Anal. Biochem.* (1983) 65:269–271. Paragon analysis of the immunoglobulins and double-diffusion Ouchterlony analysis showed that all the immunoglobulins were of the type IgM.

ELISA Assay for Oncostatin-A

Oncostatin-A was diluted in 0.1M acetic acid and 10 ng/well was pipetted into a 96 well Dynatech Immulon plate. The solution was dried down overnight at room temperature. The plate was blocked by incubation of the wells with 2.5% BSA, 2.5% fetal bovine serum (FCS) in PBS at 37° C. for 1 hr. The plate was then washed twice with 2.5% FCS in PBS. The hybridoma medium, immunoglobulin or antiserum was then added at the appropriate dilution. The plates were then incubated at 37° C. for two hours and washed three times with 2.5% FCS in PBS. Vector labs avidin-biotin-HRP ELISA reagents were used according to the manufacturers directions. The wells were washed with 2.5% FCS in PBS between each step. The positive wells were visualized by the addition of 0.4 mg/ml orthophenylenediamine in 0.1M sodium citrate solution containing 4 μl of 30% hydrogen peroxide/10 ml of solution. The reaction was allowed to continue for 30 min at room temperature. The reaction was stopped by the addition of 50 μl 1.4N $H_2SO_4$/well.

Production of Polyclonal Anti-Oncostatin Antiserum

Balb/c mice were immunized with nitrocellulose immobilized Oncostatin-A. The purpose of this immunization protocol is to avoid rapid clearance of the polypeptide by the host. In this way, immunization can be effected by very small amount of Oncostatin-A.

A solution of Oncostatin-A in 0.1M acetic acid was dotted onto small pieces of nitrocellulose (Schleicher & Schuell, 0.45 μm) and allowed to dry. The pieces of nitrocellulose were placed into the peritoneal cavity of three Balb/c mice for the initial immunization (0.375 ng/mouse). (The mice were also given a intraperitoneal injection of 0.1 ml complete Freund's adjuvant.) The mice were boosted twice at two-week intervals with Oncostatin immobilized nitrocellulose. For boosts, the nitrocellulose was chopped up, homogenized with 0.1 ml water and 0.1 ml incomplete Freund's adjuvant and injected subcutaneously (0.125 ng/mouse). The mouse sera were tested for specificity against Oncostatin-A by the ELISA assay previously described, with horseradish peroxidase conjugated protein A used as the second step reagent. The sera were tested agains Oncostatin-A peptide—KLH conjugate and a blocked plate to show specificity.

The following sequence was prepared in accordance with conventional ways:

```
            NcoI                              PstI
BssHII                         BglIII
   GG TAC CTT CGA CTT CTT CTG CCT CTA GAC GTC ACG
   CGC GCC ATG GAA GCT GAA GAA GAC GGA GAT CTG CAG TGC        -39
      /met  glu  ala  glu  glu  asp  gly  asp  leu  gln  cys
    NH2

StuI
   GAC ACG CAT TTT TGA TGA AGA GTC CAT TCC GGA GCA GTG
   CTG TGC GTA AAA ACT ACT TCT CAG GTA AGG CCT CGT CAC        -78
   leu  cys  val  lys  thr  thr  ser  gln  val  arg  pro  arg  his XhoI              NaeI
   TAG TGT AGT GAG CTC CAT TAG TTT CGG CCG GGC GTG ACG GGC
   ATC ACA TCA CTC GAG GTA ATC AAA GCC GGC CCG CAC TGC CCG    -120
   ilu  thr  ser  leu  glu  val  ilu  lys  ala  gly  pro  his  cys  pro PvuII     NruI
   TGA CGA GTC GAC TAG CGC TGA GAC TTT TTG CCA GCA TTC
   ACT GCT CAG CTG ATC GCG ACT CTG AAA AAC GGT CGT AAG        -159
   thr  ala  gln  leu  ilu  ala  thr  leu  lys  asn  gly  arg  lys BglII XbaI        PstI
   TAG ACA GAT CTG GAC GTC CGA GGC GAC ATG TTT TTT TAG
   ATC TGT CTA GAC CTG CAG GCT CCG CTG TAC AAA AAA ATC
   ilu  cys  leu  asp  leu  gln  ala  pro  leu  tyr  lys  lys  ilu AflII     BamHI
   TAG TTT TTT GAC GAC CTT AGA ATT CCT AG
   ATC AAA AAA CTG CTG GAA TCT TAA C                          -223
   ilu  lys  lys  leu  leu  glu  ser  ***
                              \
                               COOH
```

The sequence is designed for usage in *E. coli* and a number of restriction enzyme recognition sites were devised to allow for ease of modification of the coding sequence. Single stranded overlapping sequences were prepared, combined in an annealing medium and ligated to provide the complete gene with appropriate termini for insertion into an expression vector in reading phase to prepare a fused protein from which Oncostatin-A could be isolated. The single stranded segments are 5'-phosphorylated with T4 polynucleotide ligase and annealed by combining 200 pmoles of each segment in a 30 μl reaction volume (30 mM ATP, 10 mM DDT, 10 mM $MgCl_2$, 1 μg/ml spermidine, 100 mM tris-HCl, pH 7.8 and T4 DNA ligase. The dsDNA is digested with BssHII and BamHI and purified on a 7% native polyacrylamide gel.

The plasmid ptrpED5-1 (Hallewell and Entage, *Gene* (1980) 9:27; Tacon et al., *Mol. Gen. Genet.* (1980) 177:427) is digested with endonucleases BssHII and BamHI and a substantially full length fragment lacking the trp D gene and having a truncated trp E gene is isolated by preparative gel electrophoresis.

The Oncostatin-A gene is ligated to the linearized ptrpED5-1 plasmid to provide plasmid ptrp(Onc-A) and the ligation mixture is used to transform *E. coli* HB101 cells. Transformants are selected by ampicillin resistance and the plasmids analyzed by restriction endonuclease digestion. The transformants are grown at 37° C. to about $10^8$ cells/ml in Luria broth and 3-indolylacetic acid (IAA) is added to about 1 mM and growth continued for about 1 hr. Aliquots (1 ml) are centrifuged for a few seconds in an Eppendorf centrifuge and the pellets are suspended in 500 μl of 7% formic acid containing 5 mg/ml cyanogen bromide. After 24 hr at room temperature, aliquots are diluted tenfold in water and the diluted samples assayed for Oncostatin-A. Since Oncostatin-A has no internal methionine, having an N-terminal methionine cleavage of the fused protein provides Oncostatin-A having the same amino acid sequence as naturally occurring Oncostatin-A.

It is evident from the above results that the subject compounds find a wide variety of applications. Particularly, the compounds can be used in the diagnosis and treatment of neoplastic states. In therapy, the compounds can provide for the slowing of tumor cell growth, so as to be used jointly with other modes of treatment for the destruction of tumor cells. For diagnosis, the subject compounds are found to induce the production of p52, so that upon administration of the subject compounds to a host, enhanced levels of p52 would be indicative of the presence of tumor cells. This can be very important during the treatment of a neoplastic state to determine whether the removal of the tumor cells has been successful or metastases have occurred. The subject compounds can also be used as reagents in diagnostic assays for the presence of Oncostatin-A or Oncostatin-A receptors.

Although the foregoing invention has been described in some detail by way of illustration and example for purposes of clarity of understanding, it will be obvious that certain changes and modifications may be practiced within the scope of the appended claims.

What is claimed is:

1. Monoclonal antibodies specific for a composition having the sequence:

Glu Ala Glu Glu Asp Gly Asp Leu Gln Cys Leu Cys Val Lys
Thr Thr Ser Gln Val Arg Pro Arg His Ile Thr Ser Leu Glu
Val Ile Lys Ala Gly Pro His Cys Pro Thr Ala Gln Leu Ile
Ala Thr Leu Lys Asp Gly Arg Lys Ile Cys Leu Asp Leu Gln
Ala Pro Leu Tyr Lys Lys Ile Ile Lys Lys Leu Leu Glu Ser

2. Labeled monoclonal antibodies according to claim 1.

* * * * *

UNITED STATES PATENT AND TRADEMARK OFFICE
CERTIFICATE OF CORRECTION

PATENT NO. : 4,737,580
DATED : April 12, 1988
INVENTOR(S) : Twardzik et al.

It is certified that error appears in the above-identified patent and that said Letters Patent is hereby corrected as shown below:

Col. 14, lines 46 and 48 of Table I, replace "log$_{10}$ng" with --ng--, and "0.26" with --2.6--.

Signed and Sealed this

Ninth Day of April, 1991

Attest:

HARRY F. MANBECK, JR.

Attesting Officer

Commissioner of Patents and Trademarks